(12) United States Patent
Liu et al.

(10) Patent No.: US 10,858,299 B2
(45) Date of Patent: Dec. 8, 2020

(54) REVERSE ACID AND HYDROCARBON CASCADING IN ALKYLATION

(71) Applicant: LUMMUS TECHNOLOGY LLC, Bloomfield, NJ (US)

(72) Inventors: Zan Liu, Katy, TX (US); Peter Loezos, Sugar Land, TX (US); Jackeline Medina, The Woodlands, TX (US); Romain Lemoine, Bloomfield, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/401,595

(22) Filed: May 2, 2019

(65) Prior Publication Data

US 2019/0338201 A1 Nov. 7, 2019

Related U.S. Application Data

(60) Provisional application No. 62/667,023, filed on May 4, 2018.

(51) Int. Cl.
*C07C 2/62* (2006.01)
*B01J 19/24* (2006.01)

(52) U.S. Cl.
CPC .............. *C07C 2/62* (2013.01); *B01J 19/245* (2013.01)

(58) Field of Classification Search
None
See application file for complete search history.

(56) References Cited

U.S. PATENT DOCUMENTS

| | | | | |
|---|---|---|---|---|
| 2,438,852 A | * | 3/1948 | Goldsby | C07C 2/62 585/706 |
| 2,920,124 A | * | 1/1960 | Stiles | C07C 2/54 585/720 |

(Continued)

FOREIGN PATENT DOCUMENTS

| | | |
|---|---|---|
| CN | 106281432 A | 1/2017 |
| JP | 2004-538270 A | 12/2004 |
| JP | 2005-272684 A | 10/2005 |

OTHER PUBLICATIONS

International Search Report issued in corresponding International Application No. PCT/US2019/029887 dated Aug. 13, 2019 (3 pages).

(Continued)

*Primary Examiner* — Philip Y Louie
(74) *Attorney, Agent, or Firm* — Osha Bergman Watanabe & Burton LLP

(57) ABSTRACT

A cascade reactor scheme with acid and hydrocarbon flowing in reverse directions. The systems and processes for alkylation of olefins herein may include providing a first olefin to a first alkylation zone, and a second olefin to a second alkylation zone. Isoparaffin may be provided to the first alkylation zone. The isoparaffin and first olefin may be contacted with a partially spent sulfuric acid in the first alkylation zone to form a spent acid phase and a first hydrocarbon phase including alkylate and unreacted isoparaffin. The first hydrocarbon phase and second olefin may be contacted with a sulfuric acid feed in the second alkylation zone to form a second hydrocarbon phase, also including alkylate and unreacted isoparaffin, and the partially spent sulfuric acid that is fed to the first alkylation zone. Further, the second hydrocarbon phase may be separated, recovering an isoparaffin fraction and an alkylate product fraction.

22 Claims, 4 Drawing Sheets

(56) References Cited

U.S. PATENT DOCUMENTS

| | | | | |
|---|---|---|---|---|
| 3,683,041 A | | 8/1972 | Goldsby | |
| 3,760,028 A | * | 9/1973 | Francis | C07C 2/62 |
| | | | | 585/703 |
| 4,260,846 A | * | 4/1981 | Karsay | C07C 2/54 |
| | | | | 585/730 |
| 2007/0299292 A1 | * | 12/2007 | Cross | C10G 29/205 |
| | | | | 585/720 |
| 2009/0287033 A1 | * | 11/2009 | Strauss | B01J 19/0013 |
| | | | | 585/714 |
| 2010/0076241 A1 | | 3/2010 | Loescher et al. | |

OTHER PUBLICATIONS

Written Opinion issued in corresponding International Application No. PCT/US2019/029887 dated Aug. 13, 2019 (4 pages).

* cited by examiner

REVERSE ACID AND HYDROCARBON CASCADING IN ALKYLATION

BACKGROUND

Isoparaffin-olefin alkylation processes are the key route to the production of highly branched hydrocarbons with high octane numbers. Alkylation is the reaction of paraffins, usually isoparaffins, with an olefin in the presence of a strong acid which produces paraffins, e.g., of higher octane number than the starting materials and which boil in the range of gasolines. In petroleum refining, the alkylation reaction is generally the reaction of a $C_3$ to $C_5$ olefin with isobutane and/or isopentane. In refining alkylation, hydrofluoric or sulfuric acid catalysts are commonly used. In a typical process, the reaction is carried out in a reactor where the hydrocarbon reactants are dispersed into a continuous acid phase.

During the alkylation process, water, acid soluble oil (ASO) and other chemical intermediates from olefin reactions dilute the acid. Thus, a continuous acid flow is needed to maintain the desired acid concentration and purge the water, ASO and acid-soluble intermediates. There is a strong need to lower acid consumption and operating costs associated with acid-handling and spent acid regeneration.

Also during the alkylation process, alkyl sulfate is formed. If the sulfates are not removed, they will cause corrosion and fouling in downstream equipment, and also contribute to high sulfur in alkylate product.

SUMMARY OF THE DISCLOSURE

Embodiments herein relate to systems and processes for the alkylation of olefins with isoparaffins in the presence of sulfuric acid. More particularly embodiments herein relate to alkylation process schemes wherein the olefins are processed in separate reactors, with acid and hydrocarbon cascading between the reactors in a reverse direction. Embodiments herein have been found to lower acid consumption, increase alkylate octane, reduce utility requirements, and lower the sulfur concentration in the resulting alkylate product.

In one aspect, embodiments disclosed herein relate to a process for producing alkylate from C3 to C5 hydrocarbons. The process for the alkylation of olefins may include: providing a first olefin to a first alkylation zone; providing a second olefin to a second alkylation zone, wherein the second olefin may be the same or different than the first olefin; and providing an isoparaffin to the first alkylation zone. The isoparaffin and the first olefin may be contacted with a partially spent sulfuric acid in the first alkylation zone under alkylation conditions to form a spent acid phase and a first hydrocarbon phase comprising alkylate and unreacted isoparaffin. The first hydrocarbon phase and the second olefin may be contacted with a sulfuric acid feed in the second alkylation zone under alkylation conditions to form a second hydrocarbon phase, comprising alkylate and unreacted isoparaffin, and the partially spent sulfuric acid fed to the first alkylation zone. Further, the second hydrocarbon phase may be separated to recover an isoparaffin fraction and an alkylate product fraction.

In some embodiments, an isoparaffin to olefin mole ratio in the total feed to the first reaction zone is greater than an isoparaffin to olefin mole ratio in the total feed to the second reaction zone. In other embodiments, an isoparaffin to olefin mole ratio in the total feed to the first reaction zone is at least 1.5 times an isoparaffin to olefin mole ratio in the total feed to the second reaction zone. In yet other embodiments, an isoparaffin to olefin mole ratio in the total feed to the first reaction zone is at least 1.75 times an isoparaffin to olefin mole ratio in the total feed to the second reaction zone. In still further embodiments, an isoparaffin to olefin mole ratio in the total feed to the first reaction zone is at least 2 times an isoparaffin to olefin mole ratio in the total feed to the second reaction zone.

In some embodiments, the alkylation conditions in the first and second alkylation zones include a reaction temperature of the first alkylation zone that is less than a reaction temperature of the second alkylation zone. The first olefin may include C3 and/or C4 and/or C5 olefins, and the second olefin may include C3 and/or C4 and/or C5 olefins.

In some embodiments, the processes herein may further include feeding isoparaffin to the second alkylation zone. Additionally or alternatively, process herein may include feeding acid to the first alkylation zone directly.

In another aspect, embodiments disclosed herein relate to a process for producing alkylate from C3 to C5 hydrocarbons. The process for the alkylation of olefins may include: providing a C5 olefin-containing feed to a first alkylation zone; providing a C4 olefin-containing feed to a second alkylation zone; and providing a C3 olefin-containing feed to a third alkylation zone. An isoparaffin may be provided to the first alkylation reactor. The isoparaffin and the C5 olefin may be contacted with a second partially spent sulfuric acid in the first alkylation zone under alkylation conditions to form a spent acid phase and a first hydrocarbon phase comprising alkylate and unreacted isoparaffin. The first hydrocarbon phase and the C4 olefin may be contacted with a first partially spent sulfuric acid in the second alkylation zone under alkylation conditions to form a second hydrocarbon phase, comprising alkylate and unreacted isoparaffin, and the second partially spent sulfuric acid fed to the first alkylation zone. The second hydrocarbon phase and the C3 olefin may be contacted with a fresh sulfuric acid feed in the third alkylation zone under alkylation conditions to form a third hydrocarbon phase, comprising alkylate and unreacted isoparaffin, and the first partially spent sulfuric acid fed to the second alkylation zone. The third hydrocarbon phase may be separated to recover an isoparaffin fraction and an alkylate product fraction.

In some embodiments, an isoparaffin to olefin mole ratio in the total feed to the first reaction zone may be greater than an isoparaffin to olefin mole ratio in the total feed to the second reaction zone, and an isoparaffin to olefin mole ratio in the total feed to the second reaction zone may be greater than an isoparaffin to olefin mole ratio in the total feed to the third reaction zone $(I_{R1}:O_{R1} > I_{R2}:O_{R2} > I_{R3}:O_{R3})$. In other embodiments, the alkylation conditions in the first and second alkylation zones include a reaction temperature of the first alkylation zone that is less than a reaction temperature of the second alkylation zone, and the alkylation conditions in the second and third alkylation zones include a reaction temperature of the second alkylation zone that is less than a reaction temperature of the third alkylation zone $(T_{R1} > T_{R2} > T_{R3})$.

In some embodiments, processes herein may further include feeding isoparaffin to the second alkylation zone and/or the third alkylation zone. Additionally or alternatively, processes herein may include feeding acid to the first alkylation zone and/or the second alkylation zone directly. The process may further comprise maintaining an acid strength for the total acid feed to the first alkylation zone less than an acid strength for the total acid feed to the third alkylation zone.

In one aspect, embodiments disclosed herein relate to a process for producing alkylate from C3 to C5 hydrocarbons. The process for the alkylation of olefins may include: providing a C5 olefin-containing feed to a first alkylation zone; providing a C4 olefin-containing feed to a second alkylation zone; providing a C3 olefin-containing feed to a third alkylation zone; and providing an isoparaffin to the first alkylation reactor. The isoparaffin and the C5 olefin may be contacted with a first partially spent sulfuric acid in the first alkylation zone under alkylation conditions to form a second partially spent acid phase and a first hydrocarbon phase comprising alkylate and unreacted isoparaffin. The first hydrocarbon phase and the C4 olefin may be contacted with the second partially spent sulfuric acid in the second alkylation zone under alkylation conditions to form a second hydrocarbon phase, comprising alkylate and unreacted isoparaffin, and a spent sulfuric acid. The second hydrocarbon phase and the C3 olefin may be contacted with a fresh sulfuric acid feed in the third alkylation zone under alkylation conditions to form a third hydrocarbon phase, comprising alkylate and unreacted isoparaffin, and the first partially spent sulfuric acid fed to the first alkylation zone. The third hydrocarbon phase may be separated to recover an isoparaffin fraction and an alkylate product fraction.

In another aspect, embodiments disclosed herein relate to a system for producing alkylate from C3 to C5 hydrocarbons. The systems for the alkylation of olefins may include: a first flow line for providing a first olefin to a first alkylation zone; a second flow line for providing a second olefin to a second alkylation zone, wherein the second olefin may be the same or different than the first olefin; and a third flow line for providing an isoparaffin to the first alkylation zone. A first alkylation zone may be used for contacting the isoparaffin and the first olefin with a partially spent sulfuric acid under alkylation conditions to form a spent acid phase and a first hydrocarbon phase comprising alkylate and unreacted isoparaffin. A second alkylation zone may be provided for contacting the first hydrocarbon phase and the second olefin with a fresh sulfuric acid feed under alkylation conditions to form a second hydrocarbon phase, comprising alkylate and unreacted isoparaffin, and the partially spent sulfuric acid fed to the first alkylation zone. Further, systems herein may include a separator for separating the second hydrocarbon phase to recover an isoparaffin fraction and an alkylate product fraction.

In another aspect, embodiments disclosed herein relate to a system for producing alkylate from C3 to C5 hydrocarbons. The system for the alkylation of olefins may include a first alkylation zone for contacting an isoparaffin feed and a C5 olefin-containing feed with a second partially spent sulfuric acid under alkylation conditions to form a spent acid phase and a first hydrocarbon phase comprising alkylate and unreacted isoparaffin. The system may also include a second alkylation zone for contacting the first hydrocarbon phase and a C4 olefin with a first partially spent sulfuric acid under alkylation conditions to form a second hydrocarbon phase, comprising alkylate and unreacted isoparaffin, and the second partially spent sulfuric acid fed to the first alkylation zone. Further, the system may include a third alkylation zone for contacting the second hydrocarbon phase and the C3 olefin with a fresh sulfuric acid feed under alkylation conditions to form a third hydrocarbon phase, comprising alkylate and unreacted isoparaffin, and the first partially spent sulfuric acid fed to the second alkylation zone. Further, a separator may be provided for separating the third hydrocarbon phase to recover an isoparaffin fraction and an alkylate product fraction.

In yet another aspect, embodiments disclosed herein relate to a system for producing alkylate from C3 to C5 hydrocarbons. The system for the alkylation of olefins may include: a flow line for providing a C5 olefin-containing feed to a first alkylation zone; a flow line for providing a C4 olefin-containing feed to a second alkylation zone; and a flow line for providing a C3 olefin-containing feed to a third alkylation zone. The system further includes: a first alkylation zone for contacting an isoparaffin and the C5 olefin with a first partially spent sulfuric acid under alkylation conditions to form a second partially spent acid phase and a first hydrocarbon phase comprising alkylate and unreacted isoparaffin; a second alkylation zone for contacting the first hydrocarbon phase and the C4 olefin with the second partially spent sulfuric acid under alkylation conditions to form a second hydrocarbon phase, comprising alkylate and unreacted isoparaffin, and a spent sulfuric acid fed; and, a third alkylation zone for contacting the second hydrocarbon phase and the C3 olefin with a fresh sulfuric acid feed under alkylation conditions to form a third hydrocarbon phase, comprising alkylate and unreacted isoparaffin, and the first partially spent sulfuric acid fed to the first alkylation zone. Further, the system may include a separator for separating the third hydrocarbon phase to recover an isoparaffin fraction and an alkylate product fraction.

Other aspects and advantages will be apparent from the following description and the appended claims.

DETAILED DESCRIPTION

Figure 1:
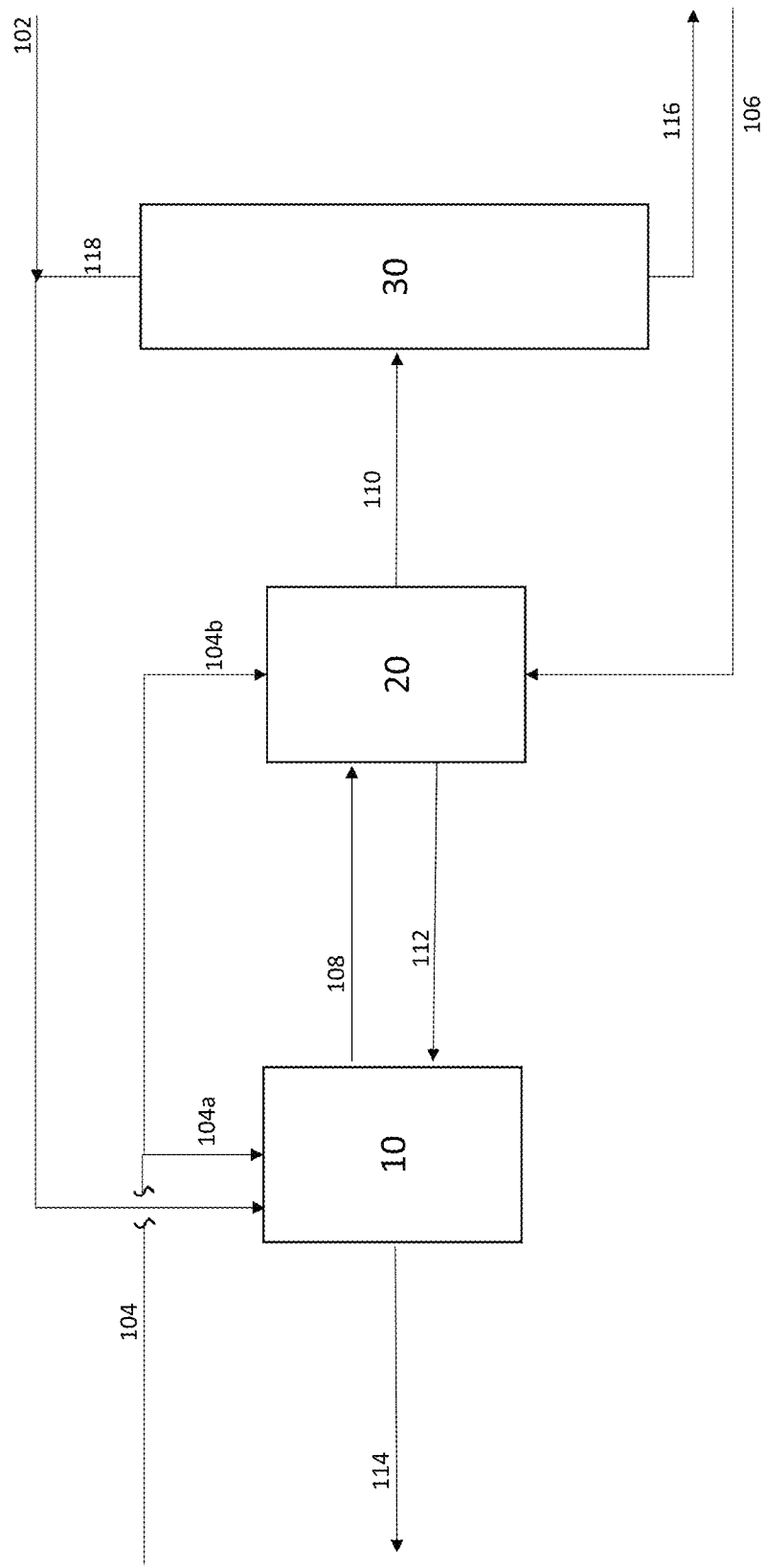
FIG. 1 is a simplified process flow diagram of an alkylation system according to embodiments herein.

Embodiments herein relate to a cascade reactor scheme with acid and hydrocarbon flowing in a reverse direction. By reverse cascading hydrocarbon and acid, the proposed reactor scheme can lower acid consumption, reduce sulfur concentration in alkylate, and improve alkylate octane.

"Acid consumption" as used herein relates to the dilution of the acid catalyst by acid soluble oils formed by undesirable side reactions. Additionally, formation of stable intermediates, such as sulfate esters when utilizing sulfuric acid catalyst, also dilute the catalyst causing an apparent acid consumption increase. "Acid strength" as used herein refers to the concentration of the acid catalyst, which for sulfuric acid is expressed in weight percent $H_2SO_4$ as determined by titration with standardized sodium hydroxide.

Alkylation feedstocks used in embodiments disclosed herein may include mixtures of various olefins and paraffins. For example, alkylation feedstocks may include $C_1$-$C_5$ paraffins, including n-alkanes and iso-alkanes, and $C_2$-$C_5$ olefins. Olefins may include n-olefins (straight chain olefins), iso-olefins (branched olefins), and mixtures thereof. In certain embodiments, paraffins may include propane, $C_4$ alkanes (n-butane and isobutane), $C_5$ alkanes (n-pentane, neopentane, and isopentane), and mixtures thereof. In some embodiments, high purity isoparaffins, such as isobutane and/or isopentane, are used as the paraffin feed. In some embodiments, alkylation feedstocks may include a $C_3$-$C_5$ light cracked naphtha (LCN) cut. In still yet another embodiment, the present invention relates to isoparaffin alkylation utilizing separately, C3, C4 and C5 olefin feedstocks.

In certain embodiments, paraffins may include $C_4$ alkanes (n-butane and isobutane), $C_5$ alkanes (n-pentane, neopentane, and isopentane), and mixtures thereof. In other embodiments, olefins may include ethylene, propylene, $C_4$ olefins (such as 1-butene, 2-butene, isobutylene, or mixtures thereof), $C_5$ olefins (such as 1-pentene, 2-pentene, isopentenes, and mixtures thereof), and mixtures thereof.

The propylene feedstock, in some embodiments, may be a mixture of propylene and propane, such as a propylene stream containing greater than 50 wt. % propylene in propane, or a mixture of C3 and C4, such as a propylene stream containing greater than 40 wt. % propylene on olefin basis.

In some embodiments, a butylene-containing feedstock may have greater than 50 wt % butylene. In some embodiments, a pentene-containing feedstock may have greater than 50 wt % pentene.

It is generally believed that reducing spending acid strength will reduce acid consumption, as lower acid strength extends the dilution range of acid, allowing purge of ASO at higher concentration. However, at lower acid strength, the ASO formation increases which offset this benefits or even reverse the benefits, leading to a higher acid consumption. To fully utilize the benefits of low spent acid strength, it has been found that adding an intermediate acid stage (Acid Cascading) can lower the impact of the low strength stage on acid consumption.

Acid cascading can reduce acid consumption. But in the low acid strength reactor, the hydride transfer rate is slower. As a result, the concentration of intermediates in the acid phase may increase, and the reaction selectivity goes lower, leading to a higher concentration of sulfur in alkylate, and reduced alkylate octane. As a remedy, the lower acid strength reactor should have a higher I/O or lower temperature to compensate the adverse effect caused by the low acid strength. Cascading hydrocarbon in a reverse direction provides an effective solution.

In some embodiments, the alkylation process includes feeding isoparaffins, such as isobutane or isopentane and C3-C5 monoolefins to an alkylation reactor. The alkylation reaction may be catalyzed with sulfuric acid in excess of 80 percent in some embodiments, in excess of 88 percent in other embodiments, and in excess of 96 percent in yet other embodiments. The alkylation process includes reacting isoparaffins with olefins in the presence of a sulfuric acid catalyst in two or more reactors. The reaction products are then separated to recover a hydrocarbon-rich phase and an acid-rich phase. The hydrocarbon-rich phase may be further treated to remove sulfate esters from the hydrocarbon phase, among other downstream operations, to produce a hydrocarbon effluent which may include unreacted isoparaffin and alkylate products. The alkylation products recovered may then be separated into gasoline range components and heavier alkylate products, among other finishing processes.

Embodiments herein advantageously cascade isoparaffin flow and acid flow in reverse directions to improve product quality and decrease utilities, among other potential advantages, especially where propylene is alkylated. Take a two-reactor system as an example, olefin (C3 and/or C4 and/or C5 olefins) may be fed into two alkylation reactors in parallel. Fresh acid may be injected into the second reactor, and acid from the second reactor may then be cascaded into the first reactor. A portion of fresh acid can be added to the first reactor, if needed. For hydrocarbons, isobutane from a downstream separator, such as a deisobutanizer (DIB) for separating alkylate from unreacted isoparaffins, and most or all refrigeration recycle is injected into the first reactor, and the unreacted isobutene and alkylate product from the first reactor are then cascaded into the second reactor.

By reverse cascading the hydrocarbon flow and acid flow in a two reactor system, several benefits may be achieved. First, the acid cascading may allow a very low spent acid strength in the first reactor, while the intermediate acid stage (second reactor) reduces the impact of the low acid strength stage by reducing ASO formation in the second reactor. Compared to feeding acid in parallel, the acid cascading may lower acid consumption. Secondly, because the hydrocarbon flow is from the first to the second reactor, the first reactor has a higher isoparaffin to olefin (I/O) ratio. In the first, auto-refrigeration alkylation reactor, the higher I/O will allow a lower operating temperature. The higher I/O together with lower temperature will improve the reaction selectivity in the first reactor, which leads to an improved octane, and lower formation of intermediates and ASO. Third, the second reactor will work as an acid wash coalescer to remove the excessive sulfate formed in the lower acid strength first reactor. Fourth, compared to feeding isoparaffin in parallel, cascading the isoparaffin in series may double the I/O ratio in the first reactor as compared to the second reactor. In addition, because the second reactor can operate at a higher acid strength, a higher temperature can be employed in the second reactor, reducing the utility consumption in associated feed compressors. Overall, to achieve lower acid consumption, the reverse hydrocarbon/acid cascading is able to reduce the utility cost associated with the product separator (overhead isoparaffin recycle) and feed compressors.

The reverse cascading may also benefit segregated olefin feeds and reactor systems including three or more reactors. For example, a C3-rich olefin (>70% propylene) may be injected into reactor #3, and C4-rich and/or C5-rich olefins can be injected into reactor #1 and/or #2. For the acid flow, the fresh acid may be injected into reactor #3 (propylene alkylation), and then the partially spent acid may be cascaded into reactor #2 and/or #1 in series. The isoparaffin, such as isobutane, may be firstly injected into reactor #1 or reactor #2 depending on the feed type, feed quantity, and the feed's sensitivity to temperature, I/O ratio, and acid strength. Preferably, the bulk of the isoparaffin should be injected into a reactor along with the olefin type which is most sensitive to I/O ratio and temperature.

As a result of the acid cascading, reactor #3 may have the highest acid strength and lowest I/O. This translates into reactor #3 having the highest temperature for auto-refrigeration, which is the preferred operating condition for processing propylene-rich olefins. In addition, because of the higher acid strength in reactor #3 compared to reactor #1 and #2, all alkylate product formed in reactor #1 and reactor #2 can be acid washed in reactor #3 by a higher strength acid, before entering product separations and recovery. This higher acid strength in the last reactor of the series facilitates the removal of sulfate formed at a lower acid strength in reactor #1 and reactor #2.

Referring now to FIG. 1, a simplified process diagram of an alkylation system according to embodiments herein is illustrated. The alkylation system may include a first alkylation reaction zone 10, a second alkylation reaction zone 20, and one or more separators 30. Feeds to the reactors may include an isoparaffin feed 102, one or more olefin feeds 104, and a fresh acid feed 106.

The fresh acid 106 may be initially fed to the terminal reactor, second alkylation zone 20, and contacted with the olefin 104*b* and hydrocarbon effluent 108 recovered from the first alkylation zone 10 to convert isoparaffins and olefin to an alkylate product. The resulting reaction effluent may then be separated to recover a second hydrocarbon effluent 110 and a partially spent acid fraction 112.

Partially spent acid fraction 112 may then be fed to first reaction zone 10, where it may be contacted with the olefin 104*a* and isoparaffin feed 102 to convert the isoparaffins and olefin to an alkylate product. The resulting reaction effluent may then be separated to recover hydrocarbon effluent 108 and a spent acid fraction 114.

The above is described with respect to acid flow (second reactor first, then spent acid to the first reactor. Restating the above with respect to hydrocarbon (isoparaffin) flow, the system may include a flow stream for providing a first olefin 104(*a*) to a first alkylation zone 10 and a flow stream for providing a second olefin 104(*b*) to a second alkylation zone 20, where the second olefin 104(*b*) may be the same or different than the first olefin 104(*a*). The system may also include a flow stream 102 for providing an isoparaffin to the first alkylation zone 10.

In the first alkylation zone 10, the isoparaffin 102 and the first olefin 104(*a*) may be contacted with a partially spent sulfuric acid 112 under alkylation conditions to convert the olefin and isoparaffins to alkylate and to form a spent acid phase 114 and a first hydrocarbon phase 108 comprising alkylate and unreacted isoparaffin. In the second alkylation zone 20, the first hydrocarbon phase 108 and the second olefin may be contacted with a fresh sulfuric acid feed 106 under alkylation conditions to form a second hydrocarbon phase 110, comprising alkylate and unreacted isoparaffin, and the partially spent sulfuric acid 112, which may be fed to the first alkylation zone 10.

The resulting hydrocarbons 110 may then be fed to a separator, such as a distillation column, for separating the heavier alkylate product fraction 116 and a lighter isoparaffin fraction 118, which may be recycled to one or both of reactors 10, 20.

Figure 2:
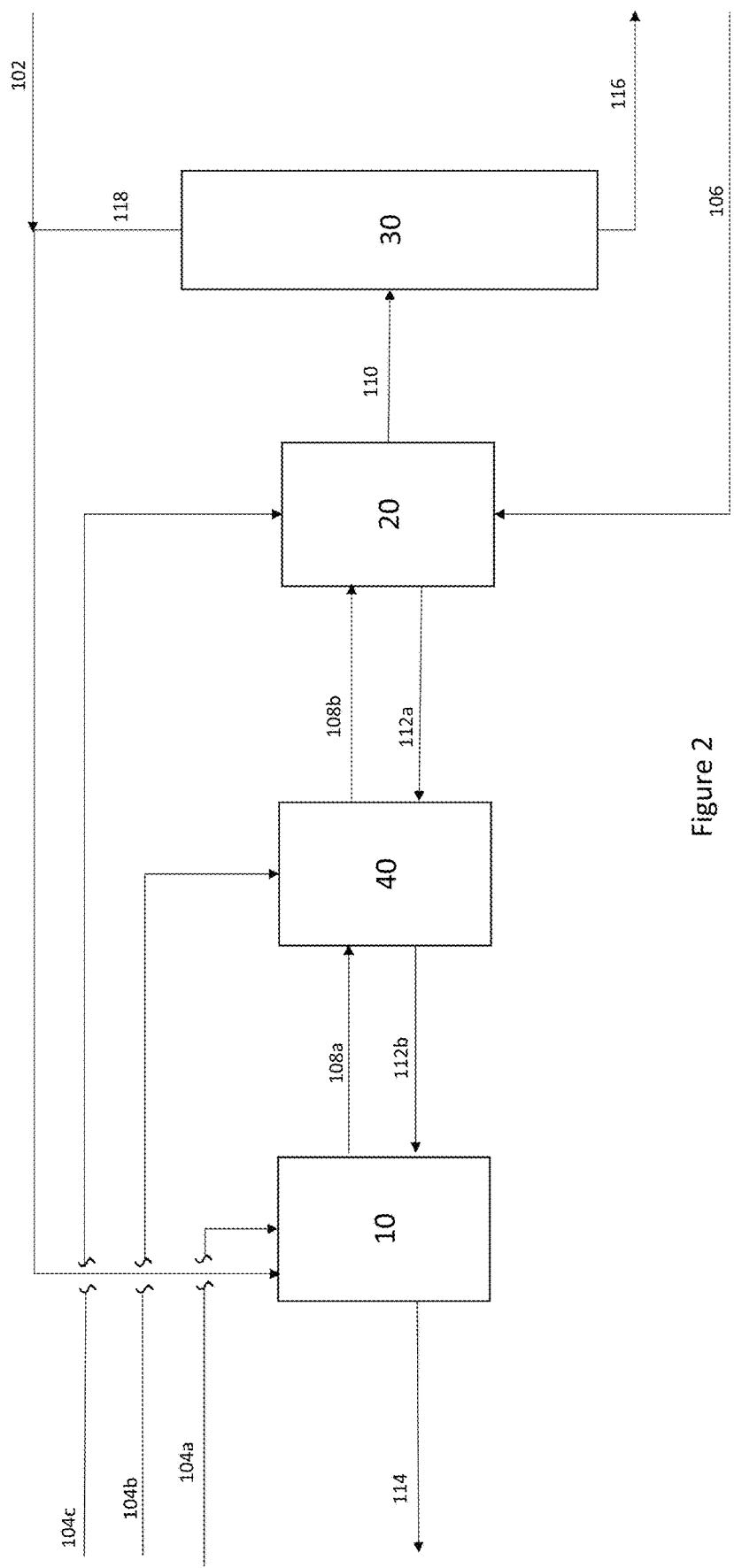
FIG. 2 is a simplified process flow diagram of an alkylation system according to embodiments herein.

Referring now to FIG. 2, a simplified process diagram of an alkylation system according to embodiments herein is illustrated, where like numerals represent like parts. The alkylation system may include a first alkylation reaction zone 10, one or more intermediate alkylation reaction zones 40, a terminal alkylation reaction zone 20, and one or more separators 30. Feeds to the reactors may include an isoparaffin feed 102, one or more olefin feeds 104*a*, 104*b*, 104*c*, and a fresh acid feed 106. In some embodiments, olefin feed 104*a* is a pentene-rich fraction, olefin feed 104*b* is a butene-rich fraction, and olefin 104*c* is a propylene fraction.

The fresh acid 106 may be initially fed to the terminal reactor, alkylation zone 20, and contacted with the olefin 104*c* and hydrocarbon effluent 108*b*, recovered from the intermediate alkylation zone 40, to convert isoparaffins and olefin to an alkylate product. The resulting reaction effluent may then be separated to recover a hydrocarbon effluent 110 and a partially spent acid fraction 112*a*.

Partially spent acid fraction 112*a* may then be fed to intermediate reaction zone 40, where it may be contacted with the olefin 104*b* and isoparaffin feed 102 to convert the isoparaffins and olefin to an alkylate product. The resulting reaction effluent may then be separated to recover hydrocarbon effluent 108 and a partially spent acid fraction 112*b*.

Partially spent acid fraction 112*b* may then be fed to first reaction zone 10, where it may be contacted with the olefin 104*a* and isoparaffin feed 102 to convert the isoparaffins and olefin to an alkylate product. The resulting reaction effluent may then be separated to recover hydrocarbon effluent 108*a* and a spent acid fraction 114.

The above is described with respect to acid flow (third reactor first, then spent acid to the second reactor, and further spent acid to the first reactor). Restating the above with respect to hydrocarbon (isoparaffin) flow, the system may include a flow stream for providing a first olefin 104(*a*), such as pentenes, to a first alkylation zone 10, a flow stream for providing a second olefin 104(*b*), such as butenes, to an intermediate or second alkylation zone 40, and a flow stream for providing a third olefin, such as propylene, to a terminal or third reaction zone 20. In some embodiments, the first olefin 104(*a*), second olefin 104(*b*), and/or the third olefin 104(*c*) may be the same or different. The system may also include a flow stream 102 for providing an isoparaffin to the first alkylation zone 10.

In the first alkylation zone 10, the isoparaffin 102 and the first olefin 104(*a*) may be contacted with a second partially spent sulfuric acid 112*b* under alkylation conditions to convert the olefin and isoparaffins to alkylate and to form a spent acid phase 114 and a first hydrocarbon phase 108*a* comprising alkylate and unreacted isoparaffin. In the second alkylation zone 40, the first hydrocarbon phase 108*a* and the second olefin may be contacted with a partially spent sulfuric acid feed 112*a* under alkylation conditions to form a second hydrocarbon phase 108*b*, comprising alkylate and unreacted isoparaffin, and the partially spent sulfuric acid 112*b*, which may be fed to the first alkylation zone 10. In the third alkylation zone 20, the second hydrocarbon phase 108*b* and the third olefin may be contacted with a fresh sulfuric acid feed 106 under alkylation conditions to form a third hydrocarbon phase 110, comprising alkylate and unreacted isoparaffin, and the partially spent sulfuric acid 112, which may be fed to the second alkylation zone 40.

The resulting hydrocarbons 110 may then be fed to a separator 30, such as a distillation column, for separating the heavier alkylate product fraction 116 from a lighter isoparaffin fraction 118, which may be recycled to one or each of reactors 10, 20, 40.

Figure 3:
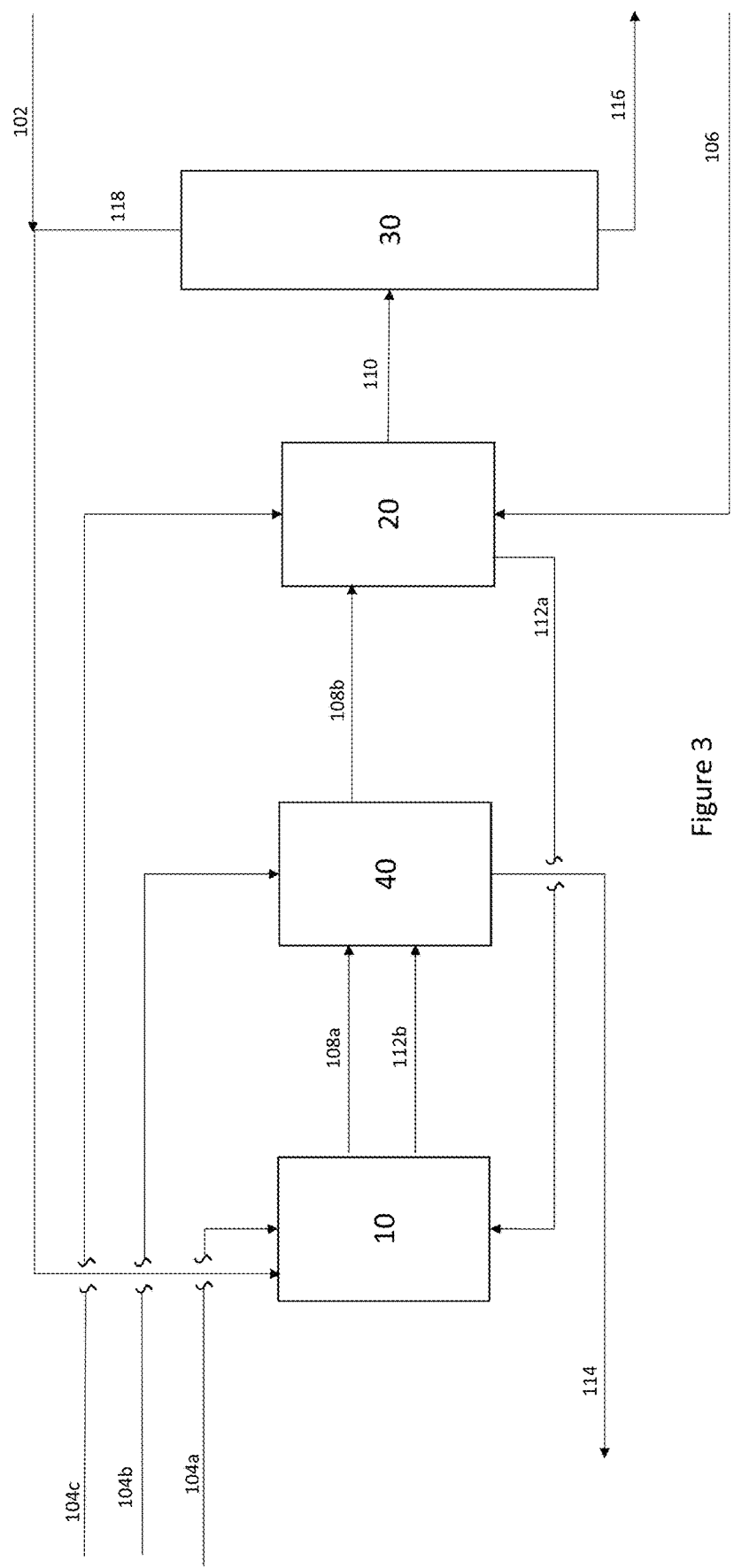
FIG. 3 is a simplified process flow diagram of an alkylation system according to embodiments herein.

In some embodiments, the advantages of a higher terminal reactor temperature may be realized where the acid flow is cascaded to an upstream reactor (relative to hydrocarbon flow), albeit not an immediately upstream reactor. Referring now to FIG. 3, a simplified process diagram of an alkylation system according to other embodiments herein is illustrated, where like numerals represent like parts.

The alkylation system illustrated in FIG. 3 may include a first alkylation reaction zone 10, one or more intermediate alkylation reaction zones 40, a terminal alkylation reaction zone 20, and one or more separators 30. Feeds to the reactors may include an isoparaffin feed 102, one or more olefin feeds 104*a*, 104*b*, 104*c*, and a fresh acid feed 106. In some embodiments, olefin feed 104*a* is a pentene-rich fraction, olefin feed 104*b* is a butene-rich fraction, and olefin 104*c* is a propylene fraction.

The fresh acid 106 may be initially fed to the terminal reactor, alkylation zone 20, and contacted with the olefin 104*c* and hydrocarbon effluent 108*b*, recovered from the intermediate alkylation zone 40, to convert isoparaffins and olefin to an alkylate product. The resulting reaction effluent may then be separated to recover a hydrocarbon effluent 110 and a partially spent acid fraction 112*a*.

Partially spent acid fraction 112*a* may then be fed to first reaction zone 10, where it may be contacted with the olefin 104*a* and isoparaffin feed 102 to convert the isoparaffins and olefin to an alkylate product. The resulting reaction effluent may then be separated to recover hydrocarbon effluent 108a and a partially spent acid fraction 112b.

Partially spent acid fraction 112b may then be fed to second reaction zone 10, where it may be contacted with the olefin 104b to convert the isoparaffins and olefin to an alkylate product. The resulting reaction effluent may then be separated to recover hydrocarbon effluent 108b and a spent acid fraction 114.

The above is described with respect to acid flow (third reactor first, then spent acid to the first reactor, and further spent acid to the second reactor). Restating the above with respect to hydrocarbon (isoparaffin) flow, the system may include a flow stream for providing a first olefin 104(a), such as pentenes, to a first alkylation zone 10, a flow stream for providing a second olefin 104(b), such as butenes, to an intermediate or second alkylation zone 40, and a flow stream for providing a third olefin, such as propylene, to a terminal or third reaction zone 20. In some embodiments, the first olefin 104(a), second olefin 104(b), and/or the third olefin 104(c) may be the same or different. The system may also include a flow stream 102 for providing an isoparaffin to the first alkylation zone 10.

In the first alkylation zone 10, the isoparaffin 102 and the first olefin 104(a) may be contacted with a first partially spent sulfuric acid 112a under alkylation conditions to convert the olefin and isoparaffins to alkylate and to form a second partially spent acid phase 112b and a first hydrocarbon phase 108a comprising alkylate and unreacted isoparaffin. In the second alkylation zone 40, the first hydrocarbon phase 108a and the second olefin may be contacted with second partially spent sulfuric acid feed 112b under alkylation conditions to form a second hydrocarbon phase 108b, comprising alkylate and unreacted isoparaffin, and spent sulfuric acid 114. In the third alkylation zone 20, the second hydrocarbon phase 108b and the third olefin may be contacted with a fresh sulfuric acid feed 106 under alkylation conditions to form a third hydrocarbon phase 110, comprising alkylate and unreacted isoparaffin, and the first partially spent sulfuric acid 112a, which may be fed to the first alkylation zone 10.

The resulting hydrocarbons 110 may then be fed to a separator 30, such as a distillation column, for separating the heavier alkylate product fraction 116 from a lighter isoparaffin fraction 118, which may be recycled to one or each of reactors 10, 20, 40.

Figure 4:
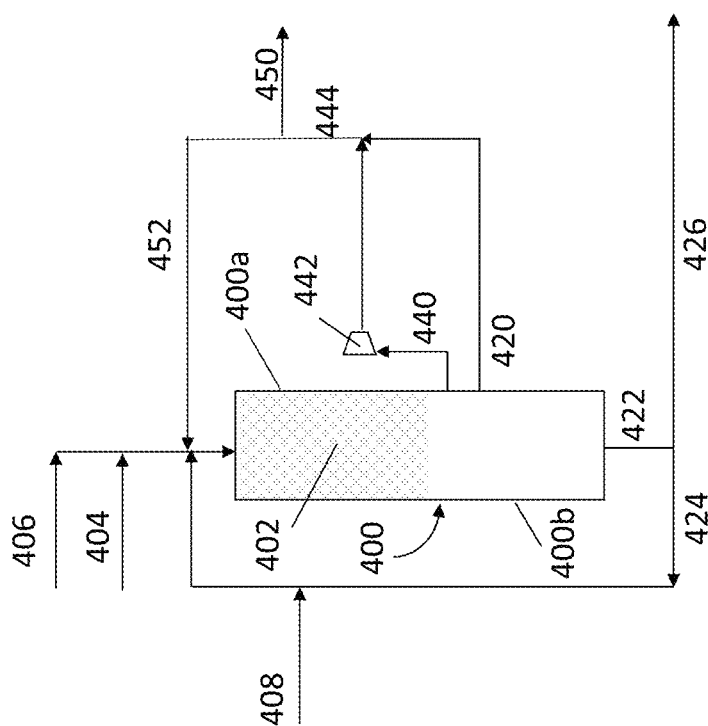
FIG. 4 is a simplified process flow diagram of an alkylation reaction zone useful with embodiments herein.

Referring now to FIG. 4, a simplified process diagram of an alkylation zone according to embodiments herein is illustrated. An alkylation zone may include a reaction zone and a separation zone. The alkylation zone 400, for example, may include an upper reaction section 400a and a bottom separation section 400b. Contact structures 402 may be positioned in upper section 400a to facilitate the intimate contact of the olefin 404, isoparaffin 406, and the sulfuric acid 408.

Conditions in the alkylation zone 400 may be maintained such that at least a portion or all of the olefin reacts with the isoparaffin to form alkylate, as mentioned above. The resulting reaction mixture may then be separated, for example, by decanting the reaction mixture in lower section 400b to recover a hydrocarbon fraction 420, including alkylate, unreacted isoparaffin, and any unreacted olefin, when present, and a spent or partially spent acid fraction 422.

If contact structures are used, they may be positioned in upper section 400a of the alkylation reactor 400 for contacting the sulfuric acid, isoparaffin and the olefin feed streams. In some embodiments, contact structures or dispersers used in embodiments described herein may include at least 50 percent void space; at least 60 percent void space in other embodiments; at least 70 percent void space in other embodiments; at least 80 percent void space in other embodiments; and up to 99 percent void space in yet other embodiments. For example, in some embodiments, a contact structure may include a multi-filament component and a structural element, such as a co-knit wire mesh, dispersers, or other suitable contact structures. For example, contact structures as described in U.S. Pat. No. 6,774,275, incorporated herein by reference, may be used.

In some embodiments, a pulse flow regime may also be used for the reaction zone of the alkylation reactors 400. The pulses may be characterized by large mass and heat transfer rates. Increased contact structure wetting and a continuous mixing between parallel flowing rivulets may diminish flow maldistribution. In addition, the formation of local hot spots may be reduced, leading to an intrinsically safer process. The pulses may continuously mobilize stagnant liquid holdup to the point where its stagnant nature disappears. Since stagnant holdup represents 10 to 30 percent of the total liquid holdup in trickle flow operations, the dynamic character of the pulse flow regime may enhance reactor performance, such as by improved radial mixing.

A portion or all of a partially spent acid fraction 422 recovered from an alkylation zone may be fed to another alkylation zone (not illustrated), as described above. In some embodiments, a portion 424 of the acid fraction 458 may also be recycled to the same alkylation reactor 400, such as to maintain a desired acid concentration in the first alkylation reactor 400. The remaining acid may be recovered as spent acid fraction 426, which may be forwarded to a different reactor or recovered for spent acid recovery.

Additionally, the heat of reaction may produce some vapors 440, which may be removed. If desired, these vapors may be condensed or compressed, such as by using a compressor 442, and combined with the recovered liquid hydrocarbon fraction 420 to form hydrocarbon fraction 444. In some embodiments, the recovered hydrocarbon fraction 444 may be split into a first portion 450 to be sent to a downstream alkylation zone or product recovery zone, and a second portion 452 may be recycled to the same alkylation reactor 400, such as to maintain a desired olefin feed concentration and/or for temperature control.

Sulfuric acid fed to the alkylation zones may include fresh and/or recycled sulfuric acid. In some embodiments, the concentration of sulfuric acid phase entering the alkylation reactors may be maintained at a concentration that titrates as below 99.8 weight percent strength sulfuric acid/water mixtures or less. In other embodiments, the sulfuric acid may be maintained at a concentration range titrating as 20 to 96 weight percent sulfuric acid/water mixtures; titrating as 25 to 75 weight percent sulfuric acid/water mixtures in other embodiments; and titrating as 30 to 70 weight percent sulfuric acid/water mixtures in yet other embodiments. It can be noted that that the acid phase in these instances is composed of sulfuric acid, sulfate esters, ASO (acid soluble oils) and water. It does not contain significant quantities of water, typically 0-5% by weight, and for the purposes of describing the acid content, the terminology "titrates as" or "titrating as" is used to indicate a sulfuric acid/water mixture which has the same acidity, understanding that the acid mixture used herein is more complex in chemical makeup. Measurement of the acidity may be measured, for example, using a METTLER DL-77 or a METTLER T-90 titrator.

In some embodiments, fresh acid may be fed in addition to the spent acid fed to the alkylation zones. The flowrates of the fresh acid streams, the portion of the recovered acid recycled to the alkylation reactor and the portion of the spent acid forwarded to another alkylation zone or to acid recovery may be controlled in order to achieve a desired or optimal acid strength in each respective alkylation reactor. As described above, the flow of acid and recycled acid may be maintained such that the acid strength in the last alkylation zone is greater than the acid strength in the upstream alkylation zones (respective to isoparaffin feed/hydrocarbon flow).

For a reaction system containing n reactors, the terminal, or last reactor (with respect to hydrocarbon flow) may have the highest acid strength. In other words, the advantageous sulfur separations may be realized where the acid strength in reactor n is greater than that used in reactors 1 to n−1 (i.e., Acid Strength$_{reactor\ n}$>Acid Strength$_{reactors\ 1\ to\ n-1}$).

In the embodiment of FIG. 1, for example, the acid strength in second alkylation zone 20 may be maintained at a concentration in the range from 80-99%, and the acid strength in first alkylation zone 10 may be maintained at a concentration in the range from 80-99%, but less than that of reactor 20. In the embodiment of FIG. 2, for example, the acid strength in third alkylation zone 20 may be maintained at a concentration in the range from 80-99%, the acid strength in second alkylation zone 40 may be maintained at a concentration in the range from 80-99%, and the acid strength in first alkylation zone 10 may be maintained at a concentration in the range from 80-99%, but less than that of reactor 20. In the embodiment of FIG. 3, for example, the acid strength in alkylation zone 20 may be maintained at a concentration in the range from 80-99%, the acid strength in alkylation zone 10 may be maintained at a concentration in the range from 80-99%, and the acid strength in alkylation zone 40 may be maintained at a concentration in the range from 80-99%, but less than that of reactor 20.

In some embodiments, a mass ratio of the sulfuric acid to the propylene feedstock fed to the propylene alkylation reactor, such as alkylation zone 20 for example, may be in the range from 0.1:1 to 30:1. In other embodiments, a mass ratio of the sulfuric acid to the propylene feedstock fed to propylene alkylation reactor may be in the range from 0.1:1 to 20:1; and in the range from 1:1 to 10:1 in yet other embodiments.

Reaction conditions for the alkylation zones may depend on the type of feed and the acid strength maintained in the reactor, as noted above. Conditions in the alkylation reactors may be maintained such that at least a portion of the olefin reacts with the isoparaffin to form alkylate, as mentioned above, while minimizing formation of heavies. For example, in some embodiments, the temperature in the alkylation reactors may be maintained in the range from −7° C. to 38° C. (20° F. to 100° F.); from −4° C. to 18° C. (25° F. to 65° F.) in other embodiments; ranging from −1° C. to 10° C. (30° F. to 50° F.) in other embodiments; and ranging from −7° C. to 4° C. (20° F. to 40° F.) in yet other embodiments. Alkylation reactor pressures may range from about 5 to about 500 psig in some embodiments; from about 10 to 250 psig in other embodiments; and from about 20 to 150 psig in yet other embodiments. The combination of temperature and pressure used in some embodiments is sufficient to maintain the feed and products in the liquid phase.

For propylene alkylation reactors, such as reactor 20 in some embodiments, reaction conditions may include a temperature in the range from 0° C. to 19° C. (32° F. to 65° F.). At these conditions, the conversion of propylene may be maximized. In some embodiments, the higher acid strength used for the propylene alkylation reactor may allow the temperature in the reactor to be higher, such as in the range from about 10° C. to about 38° C. (50° F. to 100° F.).

For a two reactor system, such as that illustrated in FIG. 1, for example, the alkylation conditions in the first and second alkylation zones include a reaction temperature of the first alkylation zone that is less than a reaction temperature of the second alkylation zone. For example, a reaction temperature in the first alkylation zone 10 may be in the range from about −7° C. to about 38° C., and the reaction temperature in the second alkylation zone 20 may be in the range from about −7° C. to about 38° C.

Likewise, for a three reactor system, the temperature in the terminal reactor (with respect to hydrocarbon flow) may be the greatest. The alkylation conditions in the first and second alkylation zones may include a reaction temperature of the first alkylation zone that is less than a reaction temperature of the second alkylation zone, and wherein the alkylation conditions in the second and third alkylation zones include a reaction temperature of the second alkylation zone that is less than a reaction temperature of the third alkylation zone ($T_{R1}$>$T_{R2}$>$T_{R3}$). In other embodiments, the alkylation conditions in the first, second, and third alkylation zones may include a reaction temperature of the first or second alkylation zone that is less than a reaction temperature of the third alkylation zone. For example, for the process as illustrated in FIG. 2, the terminal propylene alkylation reactor 30 may be operated at a temperature in the range from about −7° C. to about 38° C., whereas the first and second alkylation zones 10, 40 reacting butenes and/or pentenes may be in the range from about −7° C. to about 38° C.

In some embodiments, the olefin to isoparaffin mole ratio in the total reactor feed (for each of the alkylation reaction zones may be in the range from about 1:1.5 to about 1:30, such as from about 1:5 to about 1:15. Lower olefin to isoparaffin ratios may also be used.

For a two reactor system, for example, the isoparaffin to olefin mole ratio in the total feed to the first reaction zone (respective to isoparaffin flow) is greater than an isoparaffin to olefin mole ratio in the total feed to the second reaction zone. The terminal reactor may have the least isoparaffin to olefin mole ratio. In the embodiment of FIG. 1, for example, the isoparaffin to olefin mole ratio in the total feed to the first reaction zone 10 is greater than an isoparaffin to olefin mole ratio in the total feed to the second reaction zone 20. In some embodiments, an isoparaffin to olefin mole ratio in the total feed to the first reaction zone 10 is at least 1.5 times an isoparaffin to olefin mole ratio in the total feed to the second reaction zone 20; at least 1.75 time in other embodiments, and at least 2 times in yet other embodiments.

Likewise, for a three reactor system, an isoparaffin to olefin mole ratio in the total feed to the first reaction zone may be greater than an isoparaffin to olefin mole ratio in the total feed to the second reaction zone, and wherein an isoparaffin to olefin mole ratio in the total feed to the second reaction zone is greater than an isoparaffin to olefin mole ratio in the total feed to the third reaction zone ($I_{R1}$:$O_{R1}$>$I_{R2}$:$O_{R2}$>$I_{R3}$:$O_{R3}$). In some embodiments, an isoparaffin to olefin mole ratio in the total feed to the first reaction zone 10 may be at least 1.5 times an isoparaffin to olefin mole ratio in the total feed to the second reaction zone 40; at least 1.75 time in other embodiments, and at least 2 times in yet other embodiments Likewise, an isoparaffin to olefin mole ratio in the total feed to the second reaction zone 40 may be at least 1.5 times an isoparaffin to olefin mole ratio in the total feed to the third reaction zone 20; at least 1.75 time in other embodiments, and at least 2 times in yet other embodiments.

Similarly, for the embodiment illustrated in FIG. 3, an isoparaffin to olefin mole ratio in the total feed to the first or second reaction zones 10, 40 is greater than an isoparaffin to olefin mole ratio in the total feed to the third reaction zone 30.

Alkylation products formed according to embodiments herein may include C7 to C10 hydrocarbons. The alkylate formed using embodiments of the processes and systems disclosed herein may be used as gasoline. In some embodiments, the C7 and C8 alkylate products may be blended with other components to form a gasoline.

As described above, embodiments herein are directed toward alkylation systems with reverse cascading of hydrocarbon and acid flow. While described with respect to single reactor systems, it is envisioned that the flow may be a combination of flow-in-series and flow-in-parallel, such as where one or more of the reaction zones includes multiple reactors operating in parallel with the series flow of olefin, paraffin, and acid as described with respect to FIG. 1, 2, or 3, for example. Other embodiments are also envisioned in which reaction zones may include series and/or parallel flow within a reaction zone, but advantageously utilize the reverse cascading of acid described herein. For example, reaction zone 10 may have multiple reactors, operating in parallel with respect to the acid flow received from reactors 20 as well as the isoparaffin and/or olefin fed to the reactors. Similarly, reaction zones 20 and 40 may have multiple reactors operating in parallel with respect to the acid, isoparaffin, and olefin feeds.

Embodiments herein may advantageously provide for one or more of the following: reduced energy consumption; reduced acid consumption; increased octane of alkylate product; and reduced sulfur content in the alkylate product, among other advantages.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the alkylation of olefins, the process comprising:
   providing a first olefin to a first alkylation zone;
   providing a second olefin to a second alkylation zone, wherein the second olefin may be the same or different than the first olefin;
   providing an isoparaffin to the first alkylation zone;
   contacting the isoparaffin and the first olefin with a partially spent sulfuric acid in the first alkylation zone under alkylation conditions to form a spent acid phase and a first hydrocarbon phase comprising alkylate and unreacted isoparaffin;
   contacting the first hydrocarbon phase and the second olefin with a sulfuric acid feed in the second alkylation zone under alkylation conditions to form a second hydrocarbon phase, comprising alkylate and unreacted isoparaffin, and the partially spent sulfuric acid fed to the first alkylation zone; and
   separating the second hydrocarbon phase to recover an isoparaffin fraction and an alkylate product fraction.

2. The process of claim 1, wherein an isoparaffin to olefin mole ratio in a total feed to the first reaction zone is greater than an isoparaffin to olefin mole ratio in a total feed to the second reaction zone.

3. The process of claim 1, wherein an isoparaffin to olefin mole ratio in a total feed to the first reaction zone is at least 1.5 times an isoparaffin to olefin mole ratio in a total feed to the second reaction zone.

4. The process of claim 1, wherein an isoparaffin to olefin mole ratio in a total feed to the first reaction zone is at least 1.75 times an isoparaffin to olefin mole ratio in a total feed to the second reaction zone.

5. The process of claim 1, wherein an isoparaffin to olefin mole ratio in a total feed to the first reaction zone is at least 2 times an isoparaffin to olefin mole ratio in a total feed to the second reaction zone.

6. The process of claim 1, wherein the alkylation conditions in the first and second alkylation zones include a reaction temperature of the first alkylation zone that is less than a reaction temperature of the second alkylation zone.

7. The process of claim 1, wherein the first olefin comprises C3 and/or C4 and/or C5 olefins and wherein the second olefin comprises C3 and/or C4 and/or C5 olefins.

8. The process of claim 1, further comprising feeding isoparaffin to the second alkylation zone.

9. The process of claim 1, further comprising feeding sulfuric acid to the first alkylation zone directly.

10. A process for the alkylation of olefins, the process comprising:
    providing a C5 olefin-containing feed to a first alkylation zone;
    providing a C4 olefin-containing feed to a second alkylation zone;
    providing a C3 olefin-containing feed to a third alkylation zone;
    providing an isoparaffin to the first alkylation reactor;
    contacting the isoparaffin and the C5 olefin with a second partially spent sulfuric acid in the first alkylation zone under alkylation conditions to form a spent acid phase and a first hydrocarbon phase comprising alkylate and unreacted isoparaffin;
    contacting the first hydrocarbon phase and the C4 olefin with a first partially spent sulfuric acid in the second alkylation zone under alkylation conditions to form a second hydrocarbon phase, comprising alkylate and unreacted isoparaffin, and the second partially spent sulfuric acid fed to the first alkylation zone;
    contacting the second hydrocarbon phase and the C3 olefin with a fresh sulfuric acid feed in the third alkylation zone under alkylation conditions to form a third hydrocarbon phase, comprising alkylate and unreacted isoparaffin, and the first partially spent sulfuric acid fed to the second alkylation zone; and
    separating the third hydrocarbon phase to recover an isoparaffin fraction and an alkylate product fraction.

11. The process of claim 10, wherein an isoparaffin to olefin mole ratio in a total feed to the first reaction zone is greater than an isoparaffin to olefin mole ratio in a total feed to the second reaction zone, and wherein an isoparaffin to olefin mole ratio in a total feed to the second reaction zone is greater than an isoparaffin to olefin mole ratio in a total feed to the third reaction zone ($I_{R1}:O_{R1} > I_{R2}:O_{R2} > I_{R3}:O_{R3}$).

12. The process of claim 10, wherein the alkylation conditions in the first and second alkylation zones include a reaction temperature of the first alkylation zone that is less than a reaction temperature of the second alkylation zone, and wherein the alkylation conditions in the second and third alkylation zones include a reaction temperature of the second alkylation zone that is less than a reaction temperature of the third alkylation zone ($T_{R1} > T_{R2} > T_{R3}$).

13. The process of claim 10, further comprising feeding isoparaffin to the second alkylation zone and the third alkylation zone.

14. The process of claim 10, further comprising feeding sulfuric acid to the first alkylation zone and/or the second alkylation zone directly.

15. The process of claim 10, further comprising maintaining an acid strength for a total acid feed to the first alkylation zone less than an acid strength for a total acid feed to the third alkylation zone.

16. A process for the alkylation of olefins, the process comprising:
providing a C5 olefin-containing feed to a first alkylation zone;
providing a C4 olefin-containing feed to a second alkylation zone;
providing a C3 olefin-containing feed to a third alkylation zone;
providing an isoparaffin to the first alkylation reactor;
contacting the isoparaffin and the C5 olefin with a first partially spent sulfuric acid in the first alkylation zone under alkylation conditions to form a second partially spent acid phase and a first hydrocarbon phase comprising alkylate and unreacted isoparaffin;
contacting the first hydrocarbon phase and the C4 olefin with the second partially spent sulfuric acid in the second alkylation zone under alkylation conditions to form a second hydrocarbon phase, comprising alkylate and unreacted isoparaffin, and a spent sulfuric acid;
contacting the second hydrocarbon phase and the C3 olefin with a fresh sulfuric acid feed in the third alkylation zone under alkylation conditions to form a third hydrocarbon phase, comprising alkylate and unreacted isoparaffin, and the first partially spent sulfuric acid fed to the first alkylation zone; and
separating the third hydrocarbon phase to recover an isoparaffin fraction and an alkylate product fraction.

17. The process of claim 16, wherein an isoparaffin to olefin mole ratio in the total feed to the first or second reaction zones is greater than an isoparaffin to olefin mole ratio in the total feed to the third reaction zone.

18. The process of claim 16, wherein the alkylation conditions in the first, second, and third alkylation zones include a reaction temperature of the first or second alkylation zone that is less than a reaction temperature of the third alkylation zone.

19. The process of claim 16, further comprising feeding isoparaffin to the second alkylation zone and/or the third alkylation zone.

20. The process of claim 16, further comprising feeding acid to the first alkylation zone and/or the second alkylation zone directly.

21. A process for the alkylation of olefins, the process comprising:
providing a first olefin to a first alkylation zone;
providing a second olefin to a second alkylation zone, wherein the second olefin may be the same or different than the first olefin;
providing a third olefin to a third alkylation zone, wherein the third olefin may be the same or different than the first and/or second olefin;
providing an isoparaffin to the first alkylation zone;
contacting the isoparaffin and the first olefin with a second partially spent sulfuric acid in the first alkylation zone under alkylation conditions to form a spent acid phase and a first hydrocarbon phase comprising alkylate and unreacted isoparaffin;
contacting the first hydrocarbon phase and the second olefin with a first partially spent sulfuric acid feed in the second alkylation zone under alkylation conditions to form a second hydrocarbon phase, comprising alkylate and unreacted isoparaffin, and the second partially spent sulfuric acid fed to the first alkylation zone;
contacting the second hydrocarbon phase and the third olefin with a sulfuric acid feed in the third alkylation zone under alkylation conditions to form a third hydrocarbon phase, comprising alkylate and unreacted isoparaffin, and the first partially spent sulfuric acid fed to the second alkylation zone;
separating the third hydrocarbon phase to recover an isoparaffin fraction and an alkylate product fraction.

22. A process for the alkylation of olefins, the process comprising:
providing a first olefin to a first alkylation zone;
providing a second olefin to a second alkylation zone, wherein the second olefin may be the same or different than the first olefin;
providing a third olefin to a third alkylation zone, wherein the third olefin may be the same or different than the first and/or second olefin;
providing an isoparaffin to the first alkylation zone;
contacting the isoparaffin and the first olefin with a first partially spent sulfuric acid in the first alkylation zone under alkylation conditions to form a second partially spent acid phase and a first hydrocarbon phase comprising alkylate and unreacted isoparaffin;
contacting the first hydrocarbon phase and the second olefin with the second partially spent sulfuric acid feed in the second alkylation zone under alkylation conditions to form a second hydrocarbon phase, comprising alkylate and unreacted isoparaffin, and a spent sulfuric acid phase;
contacting the second hydrocarbon phase and the third olefin with a sulfuric acid feed in the third alkylation zone under alkylation conditions to form a third hydrocarbon phase, comprising alkylate and unreacted isoparaffin, and the first partially spent sulfuric acid fed to the first alkylation zone; and
separating the third hydrocarbon phase to recover an isoparaffin fraction and an alkylate product fraction.

* * * * *